(12) United States Patent
Pacetti

(10) Patent No.: US 7,563,454 B1
(45) Date of Patent: Jul. 21, 2009

(54) COATINGS FOR IMPLANTABLE MEDICAL DEVICES

(75) Inventor: Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1062 days.

(21) Appl. No.: 10/428,691

(22) Filed: May 1, 2003

(51) Int. Cl.
A61F 13/00 (2006.01)
(52) U.S. Cl. ...................... 424/422; 424/423
(58) Field of Classification Search ................. 424/422; 604/502; 524/17
See application file for complete search history.

(56) References Cited

U.S. PATENT DOCUMENTS

| | | | |
|---|---|---|---|
| 2,968,649 A | 1/1961 | Pailthrop et al. | |
| 3,051,677 A | 8/1962 | Roxford | |
| 3,178,399 A | 4/1965 | Lo | |
| 3,324,069 A | 6/1967 | Koblitz et al. | |
| 3,779,805 A | 12/1973 | Alsberg | |
| 3,856,827 A | 12/1974 | Catitt | |
| 4,076,929 A | 2/1978 | Dohany | |
| 4,197,380 A | 4/1980 | Chao et al. | |
| 4,304,010 A | 12/1981 | Mano | |
| 4,346,710 A | 8/1982 | Thanawalla et al. | |
| 4,353,960 A | 10/1982 | Endo et al. | |
| 4,399,264 A | 8/1983 | Squire | |
| 4,413,359 A | 11/1983 | Akiyama et al. | |
| 4,423,183 A | 12/1983 | Close | |
| 4,485,250 A | 11/1984 | Squire | |
| 4,530,569 A | 7/1985 | Squire | |
| 4,564,013 A | 1/1986 | Lilenfeld et al. | |
| 4,569,978 A | 2/1986 | Barber | |
| 4,632,842 A | 12/1986 | Karwoski et al. | |
| 4,636,346 A | 1/1987 | Gold et al. | |
| 4,718,907 A | 1/1988 | Karwoski et al. | |
| 4,733,665 A | 3/1988 | Palmaz | 128/343 |
| 4,749,585 A | 6/1988 | Greco et al. | |
| 4,754,009 A | 6/1988 | Squire | |
| 4,770,939 A | 9/1988 | Sietsess et al. | |
| 4,800,882 A | 1/1989 | Gianturco | 128/343 |
| 4,871,357 A | 10/1989 | Hsu et al. | |
| 4,876,109 A | 10/1989 | Mayer et al. | |
| 4,886,062 A | 12/1989 | Wiktor | 128/343 |
| 4,897,457 A | 1/1990 | Nakamura et al. | |
| 4,908,404 A | 3/1990 | Benedict et al. | |
| 4,910,276 A | 3/1990 | Nakamura et al. | |
| 4,931,287 A | 6/1990 | Bae et al. | |
| 4,935,477 A | 6/1990 | Squire | |
| 4,948,851 A | 8/1990 | Squire | |
| 4,973,142 A | 11/1990 | Squire | |
| 4,975,505 A | 12/1990 | Squire | |
| 4,977,008 A | 12/1990 | Squire | |
| 4,977,025 A | 12/1990 | Squire | |
| 4,977,026 A | 12/1990 | Squire | |
| 4,977,297 A | 12/1990 | Squire | |
| 4,977,901 A | 12/1990 | Ofstead | 128/772 |
| 4,982,056 A | 1/1991 | Squire | |
| 4,985,308 A | 1/1991 | Squire | |
| 4,999,248 A | 3/1991 | Squire | |
| 5,000,547 A | 3/1991 | Squire | |
| 5,006,382 A | 4/1991 | Squire | |
| 5,030,394 A | 7/1991 | Sietses et al. | |
| 5,047,020 A | 9/1991 | Hsu | |
| 5,051,114 A | 9/1991 | Nemser et al. | |
| 5,051,978 A | 9/1991 | Mayer et al. | |
| 5,053,048 A | 10/1991 | Pinchuk | |
| 5,076,659 A | 12/1991 | Bekiarian et al. | |
| 5,093,427 A | 3/1992 | Barber | |
| 5,107,852 A | 4/1992 | Davidson et al. | |
| 5,110,645 A | 5/1992 | Matsumoto et al. | |
| 5,112,457 A | 5/1992 | Marchant | 204/165 |
| 5,176,972 A | 1/1993 | Bloom et al. | |
| 5,185,408 A | 2/1993 | Tang et al. | |
| 5,246,451 A | 9/1993 | Trescony et al. | |
| 5,276,121 A | 1/1994 | Resnick | |
| 5,296,283 A | 3/1994 | Froggatt | |
| 5,302,385 A | 4/1994 | Khan et al. | |
| 5,308,685 A | 5/1994 | Froggatt | |
| 5,310,838 A | 5/1994 | Hung et al. | |
| 5,324,889 A | 6/1994 | Resnick | |
| 5,326,839 A | 7/1994 | Resnick | |
| 5,328,471 A | 7/1994 | Slepian | 604/101 |
| 5,336,518 A | 8/1994 | Narayanan et al. | |
| 5,338,608 A | 8/1994 | Resnick | |
| 5,342,348 A | 8/1994 | Kaplan | |
| 5,353,368 A | 10/1994 | Resnick | |
| 5,354,910 A | 10/1994 | Hung et al. | |
| 5,368,566 A | 11/1994 | Crocker | |

(Continued)

FOREIGN PATENT DOCUMENTS

DE 19723723 A1 12/1998

(Continued)

OTHER PUBLICATIONS

The Condensed Chemical Dictionary 10th ed. 1981, Van Nostrand Reinhold Co. pp. 32, 198.*

(Continued)

Primary Examiner—Michael G. Hartley
Assistant Examiner—James W. Rogers
(74) Attorney, Agent, or Firm—Squire Sanders & Dempsey LLP

(57) ABSTRACT

Coatings for implantable medical devices comprising non-fouling moieties or polymers chemically bonded to the surface of the device via chelating structures, and methods of fabricating the coatings are disclosed.

1 Claim, No Drawings

U.S. PATENT DOCUMENTS

| | | | |
|---|---|---|---|
| 5,380,299 A | 1/1995 | Fearnot et al. | |
| 5,383,853 A | 1/1995 | Jung et al. | |
| 5,383,928 A | 1/1995 | Scott et al. | |
| 5,395,311 A | 3/1995 | Andrews | |
| 5,403,341 A | 4/1995 | Solar | |
| 5,408,020 A | 4/1995 | Hung et al. | |
| 5,417,969 A | 5/1995 | Hsu et al. | |
| 5,443,458 A | 8/1995 | Eury | |
| 5,447,724 A | 9/1995 | Helmus et al. | |
| 5,455,040 A | 10/1995 | Marchant | 424/426 |
| 5,464,650 A | 11/1995 | Berg et al. | 427/2.3 |
| 5,545,208 A | 8/1996 | Wolff et al. | |
| 5,560,463 A | 10/1996 | Link et al. | |
| 5,562,734 A | 10/1996 | King | |
| 5,569,463 A | 10/1996 | Helmus et al. | |
| 5,575,818 A | 11/1996 | Pinchuk | |
| 5,578,073 A | 11/1996 | Haimovich et al. | 623/1 |
| 5,584,877 A | 12/1996 | Miyake et al. | 623/1 |
| 5,591,224 A | 1/1997 | Schwartz et al. | |
| 5,604,283 A | 2/1997 | Wada et al. | |
| 5,605,696 A | 2/1997 | Eury et al. | 424/423 |
| 5,616,608 A | 4/1997 | Kinsella et al. | |
| 5,628,728 A | 5/1997 | Tachibana et al. | |
| 5,632,771 A | 5/1997 | Boatman et al. | |
| 5,632,776 A | 5/1997 | Kurumatani et al. | |
| 5,632,840 A | 5/1997 | Campbell | |
| 5,635,201 A | 6/1997 | Fabo | |
| 5,667,767 A | 9/1997 | Greff et al. | 424/9.411 |
| 5,670,558 A | 9/1997 | Onishi et al. | 523/112 |
| 5,679,400 A | 10/1997 | Tuch | |
| 5,684,061 A | 11/1997 | Ohnishi et al. | |
| 5,691,311 A | 11/1997 | Maraganore et al. | |
| 5,697,967 A | 12/1997 | Dinh et al. | |
| 5,700,286 A | 12/1997 | Tartaglia et al. | 623/1 |
| 5,713,949 A | 2/1998 | Jayaraman | |
| 5,716,981 A | 2/1998 | Hunter et al. | 514/449 |
| 5,750,234 A | 5/1998 | Johnson et al. | |
| 5,758,205 A | 5/1998 | Hara et al. | 396/79 |
| 5,759,205 A | 6/1998 | Valentini | |
| 5,760,118 A | 6/1998 | Sinclair et al. | |
| 5,776,184 A | 7/1998 | Tuch | |
| 5,804,318 A | 9/1998 | Pinchuk et al. | |
| 5,820,917 A | 10/1998 | Tuch | |
| 5,824,048 A | 10/1998 | Tuch | |
| 5,824,049 A | 10/1998 | Ragheb et al. | 623/1 |
| 5,827,587 A | 10/1998 | Fukushi | |
| 5,830,178 A | 11/1998 | Jones et al. | 604/49 |
| 5,837,008 A | 11/1998 | Berg et al. | |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,858,990 A | 1/1999 | Walsh | |
| 5,860,963 A | 1/1999 | Azam et al. | |
| 5,861,168 A | 1/1999 | Cooke et al. | |
| 5,865,814 A | 2/1999 | Tuch | 604/265 |
| 5,869,127 A | 2/1999 | Zhong | |
| 5,873,904 A | 2/1999 | Ragheb et al. | 623/1 |
| 5,874,165 A | 2/1999 | Drumheller | |
| 5,879,697 A | 3/1999 | Ding et al. | |
| 5,897,911 A | 4/1999 | Loeffler | |
| 5,900,425 A | 5/1999 | Kanikanti et al. | |
| 5,911,704 A | 6/1999 | Humes | |
| 5,921,933 A | 7/1999 | Sarkis et al. | |
| 5,922,393 A | 7/1999 | Jayaraman | |
| 5,928,279 A | 7/1999 | Shannon et al. | |
| 5,932,299 A | 8/1999 | Katoot | |
| 5,945,115 A | 8/1999 | Dunn et al. | |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | |
| 6,015,541 A | 1/2000 | Greff et al. | 424/1.25 |
| 6,033,724 A | 3/2000 | Molitor | |
| 6,042,875 A | 3/2000 | Ding et al. | 427/2.24 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,534 A | 5/2000 | Ronan et al. | |
| 6,080,488 A | 6/2000 | Hostettler et al. | 428/423.3 |
| 6,090,134 A | 7/2000 | Tu et al. | |
| 6,096,070 A | 8/2000 | Ragheb et al. | 623/1 |
| 6,096,396 A | 8/2000 | Patton et al. | |
| 6,096,798 A | 8/2000 | Luthra et al. | |
| 6,096,809 A | 8/2000 | Lorcks et al. | |
| 6,099,562 A | 8/2000 | Ding et al. | 623/1.46 |
| 6,099,563 A | 8/2000 | Zhong | |
| 6,110,188 A | 8/2000 | Narciso, Jr. | 606/153 |
| 6,110,483 A | 8/2000 | Whitbourne et al. | |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,124,045 A | 9/2000 | Soda et al. | |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,179,817 B1 | 1/2001 | Zhong | |
| 6,197,051 B1 | 3/2001 | Zhong | |
| 6,203,551 B1 | 3/2001 | Wu | |
| 6,214,901 B1 | 4/2001 | Chudzik et al. | |
| 6,224,894 B1 | 5/2001 | Jamiolkowski et al. | |
| 6,231,590 B1 | 5/2001 | Slaikeu et al. | |
| 6,242,041 B1 | 6/2001 | Katoot et al. | |
| 6,254,632 B1 | 7/2001 | Wu et al. | |
| 6,258,121 B1 | 7/2001 | Yang et al. | |
| 6,262,034 B1 | 7/2001 | Mathiowitz et al. | |
| 6,273,913 B1 | 8/2001 | Wright et al. | |
| 6,299,604 B1 | 10/2001 | Ragheb et al. | |
| 6,344,035 B1 | 2/2002 | Chudzik | |
| 6,362,271 B1 | 3/2002 | Lin et al. | |
| 6,408,878 B2 | 6/2002 | Unger et al. | |
| 6,410,612 B1 | 6/2002 | Hatanaka | |
| 6,464,683 B1 | 10/2002 | Samuelson et al. | |
| 6,503,556 B2 | 1/2003 | Harish et al. | |
| 6,545,097 B2 | 4/2003 | Pinchuk et al. | |
| 6,551,708 B2 | 4/2003 | Tsuda et al. | |
| 6,716,444 B1 | 4/2004 | Castro et al. | |
| 6,746,773 B2 | 6/2004 | Llanos et al. | |
| 2001/0014717 A1 | 8/2001 | Hossainy et al. | |
| 2001/0029351 A1 | 10/2001 | Falotico et al. | |
| 2002/0051730 A1 | 5/2002 | Bodnar et al. | |
| 2002/0090389 A1 | 7/2002 | Humes et al. | |
| 2002/0094440 A1 | 7/2002 | Llanos et al. | 428/421 |
| 2002/0099438 A1 | 7/2002 | Furst | |
| 2002/0111590 A1 | 8/2002 | Davila et al. | 604/265 |
| 2002/0122877 A1 | 9/2002 | Harish et al. | |
| 2002/0123801 A1 | 9/2002 | Pacetti et al. | |
| 2002/0133183 A1 | 9/2002 | Lentz et al. | |
| 2002/0143386 A1 | 10/2002 | Davila et al. | |
| 2002/0165608 A1 | 11/2002 | Llanos et al. | |
| 2002/0188037 A1 | 12/2002 | Chudzik et al. | |
| 2003/0004563 A1 | 1/2003 | Jackson et al. | |
| 2003/0031780 A1 | 2/2003 | Chudzik et al. | |
| 2003/0039689 A1 | 2/2003 | Chen et al. | |
| 2003/0060877 A1 | 3/2003 | Falotico et al. | |
| 2003/0065346 A1 | 4/2003 | Evens et al. | |
| 2003/0065377 A1 | 4/2003 | Davila et al. | |
| 2003/0073961 A1 | 4/2003 | Happ | |
| 2003/0077312 A1 | 4/2003 | Schmulewicz et al. | |
| 2004/0063805 A1 | 4/2004 | Pacetti et al. | |
| 2004/0102758 A1 | 5/2004 | Davila et al. | |

| | | | |
|---|---|---|---|
| 2005/0288398 | A1* | 12/2005 | Messersmith et al. ......... 524/17 |

FOREIGN PATENT DOCUMENTS

| | | | |
|---|---|---|---|
| EP | 0568310 | A1 | 11/1993 |
| EP | 0623354 | A1 | 11/1994 |
| EP | 0633032 | A1 | 1/1995 |
| EP | 0 665 023 | | 8/1995 |
| EP | 0747069 | A2 | 12/1996 |
| EP | 0815803 | A1 | 1/1998 |
| EP | 0893108 | A2 | 1/1999 |
| EP | 0950385 | A2 | 10/1999 |
| EP | 0950386 | A2 | 10/1999 |
| EP | 0 970 711 | | 1/2000 |
| EP | 0968688 | A1 | 1/2000 |
| EP | 0997115 | A2 | 5/2000 |
| EP | 1 023 879 | | 8/2000 |
| EP | 1 192 957 | | 4/2002 |
| WO | WO 92/05695 | | 4/1992 |
| WO | WO 92/18320 | | 10/1992 |
| WO | WO 94/02185 | | 2/1994 |
| WO | WO 96/21404 | | 7/1996 |
| WO | WO 97/41164 | | 11/1997 |
| WO | WO 98/08463 | | 3/1998 |
| WO | WO 98/13405 | | 4/1998 |
| WO | WO 98/36784 | | 8/1998 |
| WO | WO 98/58680 | | 12/1998 |
| WO | WO 99/32051 | | 7/1999 |
| WO | WO 99/55396 | | 11/1999 |
| WO | WO 00/02599 | | 1/2000 |
| WO | WO 00/12147 | | 3/2000 |
| WO | WO 00/27455 | | 5/2000 |
| WO | WO 00/29043 | | 5/2000 |
| WO | WO 00/32255 | | 6/2000 |
| WO | WO 00/38754 | | 7/2000 |
| WO | WO 00/41738 | | 7/2000 |
| WO | WO 00/64506 | | 11/2000 |
| WO | WO 01/01890 | | 1/2001 |
| WO | WO 01/30403 | A1 | 5/2001 |
| WO | WO 01/49340 | | 7/2001 |
| WO | WO 01/87342 | A2 | 11/2001 |
| WO | WO 01/87368 | | 11/2001 |
| WO | WO 01/87372 | | 11/2001 |
| WO | WO 01/87376 | A1 | 11/2001 |
| WO | WO 02/24249 | | 3/2002 |
| WO | WO 02/26139 | A1 | 4/2002 |
| WO | WO 02/26271 | A | 4/2002 |
| WO | WO 02/26281 | A1 | 4/2002 |
| WO | WO 02/47731 | | 6/2002 |
| WO | WO 02/47732 | | 6/2002 |
| WO | WO 03/022324 | | 3/2003 |

OTHER PUBLICATIONS

The Encylopedia of Chemical Technology 5$^{th}$ ed. 1993, John Wiley & Sons, Inc. pp. 764-767.*
U.S. Appl. No. 09/966,036, filed Sep. 28, 1001, Happ.
U.S. Appl. No. 10/176,504, filed Jun. 21, 2002, Roorda et al.
U.S. Appl. No. 10/176,510, filed Jun. 21, 2002, Hossainy et al.
U.S. Appl. No. 10/177,117, filed Jun. 21, 2002, Hossainy.
U.S. Appl. No. 10/177,154, filed Jun. 21, 2002, Hossainy et al.
U.S. Appl. No. 10/198,912, filed Jul. 19, 2002, Ding et al.
U.S. Appl. No. 10/320,899, filed Dec. 16, 2002, Shah et al.
U.S. Appl. No. 10/376,348, filed Feb. 26, 2003, Ding et al.
U.S. Appl. No. 10/931,927, filed Aug. 31, 2004, Pacetti.
Anonymous, *Rolling Therapeutic Agent Loading Device for Therapeutic Agent Delivery of Coated Stent*, Research Disclousre, Publ., Hampshire, GB, No. 434, p. 975 (2000).
Arnold et al., *Effects of environment on the creep properties of a poly(ethylmethacrylate) based bone cement* J. Mater. Sci: Mater. In Med., vol. 12, pp. 707-717 (2001).
Bellex International, *CYTOP®, Amorphous Fluorocarbon Polymer*, 1 page (no date).
Bellex International, *Selected CYTOP Physical Data*, 1 page (no date).
Bellex International, *CYTOP®*, http://www.bellexinternational.com/cytop.htm, printed Mar. 30, 2001, 1 page.
Cifková et al., *Irritation effects of residual products derived from p(HEMA) gels*,Biomaterials, vol. 9, (Jul. 1998), pp. 372-375.
Dalsin et al., *DOPA: A New Anchor for PEGylation of Biomaterial Surfaces*, Soc. For Biomaterials 28$^{th}$ Annual Meeting Transactions, pp. 40 (2002).
Deb et al., *Effect of crosslinking agents on poly(ethylmethacrylate) bone cements*, J. of Mater.Sci: Mater. In Med., vol. 8, pp. 829-833 (1997).
Del Guerra et al., *In vitro biocompatibility of fluorinated polyurethanes*, J. Mater. Sci. in Med., vol. 5, pp. 452-456 (1994).
DuPont, *Telfon AF 1601S amorphous fluoropolymer solutions*, product information, 2 pages (1998).
DuPont, *Processing of Teflon® AF*, Teflon Amorphous Fluoropolymer, http://www.dupont.com/teflon/af/processing.html, printed Mar. 30, 2001, 1 page.
DuPont, *High-Performance/Potential Applications*, Teflon Amorphous Fluoropolymer, http://www.dupont.com/teflon/af/potapps.html, printed Mar. 30, 2001, 3 page.
DuPont, *Performance Comparison of Teflon AF*, Telfon Amorphous Fluoropolymer, http://www.dupont.com/teflon/af/performance.html, printed Mar. 30, 2001, 3 pages.
DuPont, *Unique Properties of Teflon® AF*, Teflon Amorphous Fluoropolymer, http://www.dupont.com/teflon/af/unique.html, printed Mar. 30, 2001, 3 pages.
DuPont, *Teflon® AF: A New Generation of High-Performance Flluropolymer Resins*, http://www.dupont.com/teflon/af/index.html, printed Mar. 30, 2001, 1 page.
DuPont, *Teflon® Protects Superconductors Against Acid*, Teflon Amorphous Fluoropolymer, http://www.dupont.com/teflon/af/superconductor.html, printed Sep. 21, 2004, 2 pages.
DuPont, *Available Grades of DuPont Teflon® AF*, Teflon Amorphous Fluoropolymer, http://www.dupont.com/teflon/af/grades.html, printed Sep. 21, 2004, 2 pages.
DuPont, *Teflon® AF amorphous fluropolymers*, Product Information 6 pages (1998).
DuPont, Sales Notice, Teflon Amorphous Fluoropolymer, http://www.dupont.com/teflon/af/patent.html, printed Sep. 21, 2004, 2 pages.
Fine et al., *Improved nerve regeneration through piezoelectric vinylidenefluoride- trifluoroethylene copolymer guidance channels*, Biomaterials, vol. 12, October, pp. 775-780 (1991).
Fischell, *Polymer Coatings for Stents*, Circulation, 94:1494-95 (1996).
Gullickson, *Reference Data Sheet on Common Chlorinated Solvents*, http://www.mcs.net/~hutter/tee/chlorina.html, printed Mar. 30, 2001, 5 pages.
Gunn et al., *Stent coatings and local drug delivery*, Eur. Heart J., vol. 20, issue 23, pp. 1693-1700 (1999).
Harpet et al., *Fatigue Characteristics of Polyethylmethacrylate Based Bone Cement Reinforced with Silane Coupled Hydroxyapatite*, Fifth World Biomaterials Congress, May 29-Jun. 2, 1996, Toronto, Canada, Abstract 351, 3 pgs.
Harper et al., *Mechanical properties of hydroxypatite reinforced poly(ethyl methacrylate) bone cement after immersion in a physiological solution: influence of a silane coupling agent*, J. Mater. Sci.: Mater. In Med., vol. 11, pp. 491-497 (2000).
Kruft et al., *Studies on radio-opaque polymeric biomaterials with potential applications to endovascular prostheses*, Biomaterials, vol. 17, No. 18, pp. 1803-1812 (1996).
Lambert et al., *Localized Arterial Wall Drug Delivery From a Polymer-Coated Removable Metallic Stent*, Circulation, vol. 90, No. 2, pp. 1003-1011 (1994).
Laroche et al., *Polyvinylidene fluoride (PVDF( as a biomaterial: From polymeric raw material to monofilament vascular suture*, J. of Biomedical Mat. Research, vol. 29, pp. 1525-1536 (1995).
Lin et al., *Fluropolymer Alloys Performance Optimization of PVDF Alloys*, Fluropolymers 2 Properties, edited by Hougham et al., Plenum Publishers N.Y. pp. 121-136 (1999).

Lin et al., *Surface characterization and platelet adhesion studies on fluorocarbons prepared by plasma-induced graft polymerization*, J. Biomater Sci. Polymer Edn., vol. 11, No. 7, pp. 701-714 (2000).

Luthra, Biointeractions Ltd. (BIL), http://www.biomateria.com/biointeractions.html, printed Sep. 21, 2004, 3 pages.

3M, *Specialty Fluids 3M™ Fluorinert™ Liquids, Typical Properties*, http://www.3m.com/market/industrial/fluids/fluoprop.html, printed Mar. 30, 2001, 3 pages.

Materials Engineering, *Applications in Design/Manufacturing/ R&D*, Materials Selector 1993, Penton Publishing (1992) 6 pgs.

Medtronic, Trillum Affinity NT, Oxygenator, Product Information, 6 pages (2000).

NCMS SOLV-DB, *Query Results for: CFC*, http://solvdb.ncms.org/CAT01.idc?chemcat=CFC, printed Mar. 30, 2001, 2 pages.

NCMS SOLV-DB, *Query Results for: FC-75 Fluorinert*, http://solvdb.ncms.org/common01.idc, printed Mar. 30, 2001, 2 pages.

Novick et al., *Protein-containing hydrophobic coatings and films*, Biomaterials, vol. 23, No. 2 (2002), pp. 441-448.

Parkell, Inc., *SNAP Powder-Liquid Temporary Crown and Bridge Resin*, http://www.parkell.com/snap.html, printed Oct. 21, 2004, 1 pg.

Parkell, Inc., *Material Safety Data Sheets*, http://www.parkell.com/msds.html, printed Oct. 21, 2004, 2 pgs.

Parkell, Inc., *MSDS No. S426, VAR, Material Safety Data Sheet*, 2 pgs (2002).

Parkell, Inc., MSDS No. S441, Material Safety Data Sheet, 2 pgs (2002).

Porté-Durrieu et al., *Surface Treatment of Biomaterials by Gamma and Swift Heavy Ions Grafting*, Nuclear Instruments and Methods in Physics Research, vol. B 151, pp. 404-415 (1999).

Porté-Durrieu et al., *Development of "Heparin-Like" Polymers Using Swift Heavy Ion and Gamma Radiation. I. Preparation and Characterization of the Materials*, Surface Treatment of Biomaterials, pp. 119-127 (2000).

Revell et al., *Experimental Studies of the Biological Response to a New Bone Cement: II Soft Tissue Reactions in the Rat*, Clinical Materials, vol. 10, pp. 233-238 (1992).

Techspray, Bulk Solvents, http://www.techspray.com/bulksup.htm, printed Sep. 21, 2004, 3 pages.

Techspray, *Flux Remover AMs*, Product Information, http://www.techspray.com/1665info.htm, printed Aug. 28, 2001, 2 pages.

Teomin et al., *Perivascular delivery of heparin for the reduction of smooth muscle cell proliferation after endothelial injury*, J. of Controlled Release, vol. 60, pp. 129-142 (1999).

Topol et al., *Frontiers in Inverventional Cardiology*, Circulation, vol. 98, pp. 1802-1820 (1998).

Urban et al., *Why Make Monofilament Sutures Out of Polyvinylidene Fluoride?*, ASAIO J., vol. 40, No. 2, pp. 145-156 (1994).

Verweire et al., *Evaluation of fluorinated polymers as coronary stent coating*, J. Mater.Sci: Mater. In Med., vol. 11, No. 4, pp. 207-212 (2000).

Weightman et al., *The Mechanical Properties of Cement and Loosening of the Femoral Components of Hip Replacements*, J. Bone and Joint Surg., vol. 69-B, No. 4, pp. 585-564 (Aug. 1987).

Wholey et al., *Global Experience in Cervical Carotid Artery Stent Placement*, Catherization and Cardiovascular Inventions, vol. 50, No. 2, pp. 160-167 (2000).

Woo et al., *Phase Behavior of Polycarbonate Blends with Selected Halogenated Polymers*, J. Appl. Polym. Sci., vol. 30, pp. 4243-4249 (1985).

International Search Report for PCT appl. PCT/US03/15347, filed May 14, 2003, date of mailing Sep. 4, 2003, 6 pgs.

International Search Report for PCT appl. PCT/US03/15544, filed May 14, 2003, date of mailing Jan. 23, 2004, 9 pgs.

International Search Report for PCT appl. PCT/US03/28643, filed Sep. 10, 2003, date of mailing Mar. 12, 2003, 10 pgs.

International Search Report for PCT appl. PCT/US03/21170, filed Jul. 2, 2003, date of mailing Oct. 31, 2003, 8 pgs.

\* cited by examiner

COATINGS FOR IMPLANTABLE MEDICAL DEVICES

BACKGROUND OF THE INVENTION

1. Field of the Invention

The present invention relates to biologically compatible, non-fouling coatings for implantable medical devices such as stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor. Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer. Once the stent has been implanted at the treatment site, the therapeutic substance has a sustained release profile from the polymer.

As a result of the implantation of bare metal stents, a low incidence of stent thrombosis can occur, even when the anti-coagulation therapy is administered before, during, and after stent implantation. Although thrombosis is only a low incidence problem for the average patient, patients having problems with blood hyper-coagulation, e.g., patients having small vessels, or those suffering from diabetes, are expected to benefit from less thrombogenic stents. Therefore, improved means of tethering anti-thrombogenic and non-thrombogenic moieties to stents is desirable.

In addition, once a bare metal stent is implanted, a thick, denatured layer of protein typically tends to accumulate on a stent surface as a result of the body's reaction to a foreign material. Such accumulation, or "fouling" of the stent surface, is undesirable from the point of view of the stent's long-term tissue compatibility. Surfaces treatments, which can reduce this chronic, foreign body reaction, to make the stent surface non-fouling or at least less fouling are, thus, beneficial. Therefore, improved means of tethering anti-fouling and non-fouling moieties to stents is also desirable.

Although local administration of therapeutic agents via stents has shown favorable results in reducing restenosis, improvements can be made to the coatings. One improvement is to have drug eluting stent coatings, and biologically compatible stent coatings that are firmly anchored to the stent surface. The embodiments of the present invention provide, among other advantages and improvements, a means of tethering biologically compatible or non-fouling polymers to bare metal stents. In addition, incorporating the compounds described in the present invention into a stent primer allows to have improved adhesion of the stent coatings to the stents.

SUMMARY

An implantable medical device is provided, the device comprising a compound a compound chemically coordinated with a surface of the device, wherein the compound includes a moiety capable of forming a chelate structure with a metal or a metal oxide, and a non-fouling moiety, conjugated to the moiety capable of forming a chelate structure. The moiety capable of forming a chelate structure includes a compound having the formula:

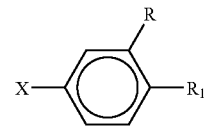

wherein each of R and $R_1$, separately, is an electron-rich group, such as hydroxyl, mercapto, phosphine, alkylphosphine, primary amino, secondary amino, tertiary amino, and carboxyl groups, and X is a reactive group such as carboxyl, mercapto, sulfonate, aldehyde, alkyl carbonyl, vinyl, acrylate, methacrylate groups, and a halogen atom. One example of a moiety capable of forming a chelate structure includes a dihydroxyphenyl moiety. The dihydroxyphenyl moiety can be derived from a derivative of pyrocatechol such as 3,4-dihydroxybenzylamine or 3,4-dihydroxyphenyl-L-alanine. A non-fouling moiety can be derived from poly(ethylene glycol), poly(ethylene oxide), poly(vinyl pyrrolidone), hyaluronic acid and its derivatives, chondroitan sulfate, dextran and its derivatives, dextrin, heparin and its derivatives, hydroxyethyl cellulose, carboxymethyl cellulose, cellulosics, or poly(vinyl alcohol).

An implantable medical device is provided, the device comprising a compound chemically coordinated with a surface of the device, wherein the compound includes a moiety capable of forming a chelate structure with a metal or a metal oxide, and a polymer conjugated to the moiety capable of forming a chelate structure. Examples of polymers which can be conjugated to the moiety capable of forming a chelate structure include poly(butyl methacrylate), poly(ethyl methacrylate), poly(methyl methacrylate), poly(vinyl alcohol), poly(ethylene-co-vinyl alcohol), poly(ethyl acetate-co-vinyl alcohol), poly(vinyl acetate), poly(ethylene-co-vinyl acetate), poly(styrene-co-ethylene), poly(styrene-co-tert-butylene), poly(vinylbutyral), poly(dimethyl siloxane), silicones, poly(tetrafluoroethylene), poly(vinyl fluoride), poly(vinylidene fluoride), poly(ethylene-co-tetrafluoroethylene), poly(vinylidene fluoride-co-hexafluoropropene), poly(styrene-block-co-ethylene-block-co-butylene), poly(styrene-block-co-butadiene-block-co-styrene), polyurethanes and polyamides.

A method for modifying an implantable medical device is also provided, the method comprises conjugating a moiety capable of forming a chelate structure to a non-fouling moiety to form the non-fouling adduct being capable of chelating, and bonding the non-fouling adduct to a surface of the device.

A method for modifying an implantable medical device is also provided, the method comprises conjugating a moiety capable of forming a chelate structure to a polymer to form a polymeric adduct, the polymeric adduct being capable of chelating, and bonding the polymeric adduct to a surface of the device.

A method for modifying an implantable medical device is also provided, the method comprises tethering a moiety capable of forming a chelate structure to a surface of the device, and bonding a first compound to the chelate structure. The first compound can include a substance having a non-fouling moiety or a polymer.

DETAILED DESCRIPTION

According to some embodiments of the present invention, stents having non-fouling properties are provided. According to other embodiments of the present invention, primers for stent coatings are provided, the primers including the chelating structures.

I. Stents Having Non-Fouling Properties

According to one embodiment of the present invention, a stent coating can contain at least one non-fouling, biologically compatible moiety. The term "non-fouling" is defined as "resisting protein adhesion or deposition, or absorbing or attracting only a minimal amount of proteins, or less proteins than a compound not having a non-fouling moiety when placed in vivo or in simulated biological fluids." The term "non-fouling moiety" is defined as a moiety carrying non-fouling properties.

To fabricate the coating having non-fouling properties, a one step or a two step process can be used. In the one step process, a chelating moiety can be chemically conjugated to a non-fouling moiety as a separate step to form a non-fouling adduct. The conjugation can be via covalent, ionic, or coordination bonds. The non-fouling adduct can then be brought into contact with the stent surface to form a bridge to the metal surface. The definition of a "chelating moiety" proposed by the International Union of Pure and Applied Chemistry (IUPAC) is used in the present application. The IUPAC defines a "chelate" as a molecular entity in which there is chelation. Chelation is defined by the IUPAC as the formation of bonds between two or more separate binding sites within the same ligand and a central atom.

In the two-step process, the first step includes forming a chelate structure by reacting the bare metal surface of the stent with the chelating moiety. The second step includes tethering a compound having non-fouling properties to the chelate structure using chemical functionality available on the chelating moiety.

An example of a suitable chelating moiety that can be used is a derivative of benzene having a reactive substituent in position 1 of the benzene ring and two electron-rich (nucleophilic) substituents in an ortho configuration. The term "ortho configuration" refers to the two electron rich substituents being located in adjacent positions of the benzene ring, such as in positions 3 and 4, or positions 2 and 3 of the ring. The role of the electron rich substituents of the benzene ring is to chemically coordinate, or chelate, with metal and/or metal oxide atoms on the stent surface. The ortho configuration places the electron-rich substituents in positions where maximum interaction of the electron-rich substituents with coordination centers on the metal surface is expected.

A structure of the chelating-moiety can be illustrated by formula (I):

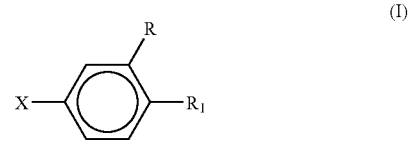

where R and $R_1$ are electron-rich groups allowing to bind the compound (I) to metal surface of a stent to form the chelate structure. In compound (I), X is in position 1, R is in position 3, and $R_1$ is in position 4 of the benzene ring; therefore, R and $R_1$ are in an ortho configuration. Examples of R and $R_1$ groups that can be used in practice of the present invention include hydroxyl, mercapto, phosphine ($-PH_2$), alkylphosphine, primary amino, secondary amino, tertiary amino, and carboxyl. Groups R and $R_1$ can be the same or different. For example, R can be hydroxyl and $R_1$ can be amino group; R can be hydroxyl and $R_1$ can be carboxyl group; or both R and $R_1$ can be hydroxyls, etc.

In the compound represented by formula (I), group X is a reactive group. Group X can be used to conjugate a non-fouling moiety to compound (I) to form a non-fouling adduct. Examples of group X that can be used include an amino group, a carboxyl group, a mercapto group, a halogen atom, such as an iodine atom, a bromine atom, or a chlorine atom, a sulfonate group, an aldehyde group, an alkyl carbonyl group, a vinyl group, an acrylate group, and a methacrylate group.

When the bare metal surface of the stent is exposed to compound (I) or to a non-fouling adduct of compound (I) with a non-fouling moiety, a chelate structure is formed, thus binding compound (I) or the non-fouling adduct to the metal surface, which can also contain metal oxide. One way of treatment of the bare metal surface of the stent is soaking the stent in a solution of compound (I) or a non-fouling adduct which includes compound (I). The duration of the soaking can be between about 5 minutes and about 24 hours, for example, about 2 hours. The solution temperature can be ambient or slightly above. The excess amount of compound (I) or the non-fouling adduct which includes compound (I), can be then removed by rinsing the stent in a suitable solvent, such as deionized water.

The solvents that can be used to form the solutions of compound (I) or the non-fouling adduct which includes compound (I) include polar solvents, for example water or water/alcohol blends. The pH of the solution of compound (I) can be between about 6 and about 8. If in compound (I) both R and $R_1$ are hydroxyl groups, the chelate structure can be illustrated as demonstrated by formula (II):

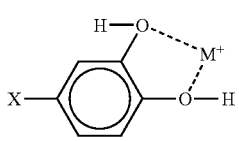

where M symbolizes a metal or a metal oxide.

In the synthetic process of attaching the non-fouling moiety to the chelating moiety, the non-fouling moiety can conjugate via the reactive group X. If the conjugating moiety is already bound to the metal surface, then the non-fouling moiety is attached to the chelate structure of formula (II).

In the step of conjugation, the reactive group X can be used for binding the non-fouling moiety. As a result, the non-fouling moiety can be tethered to the stent surface via the chelate structure (II). Examples of suitable compounds providing the non-fouling moiety include poly(ethylene glycol) (PEG), poly(ethylene oxide) (PEO), poly(vinyl pyrrolidone) (PVP), hyaluronic acid and its derivatives, chondroitan sulfate, dextran and its derivatives, dextrin, heparin and its derivatives, hydroxyethyl cellulose, carboxymethyl cellulose, cellulosics, and poly(vinyl alcohol).

Examples of compound (I) that are useful in practice of the present invention include substances where both R and $R_1$ are hydroxyl groups, as shown by formula (III):

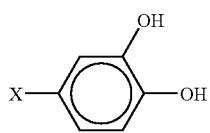

Substances shown by formula (III) are derivatives of pyrocatechol, where X can be methylamino group or L-alanine group. If X is methylamino group, compound (III) is 3,4-dihydroxybenzylamine (DHBA) shown by formula (IV), and if X is L-alanine group, compound (III) is 3,4-dihydroxyphenyl-L-alanine (DOPA) shown by formula (V):

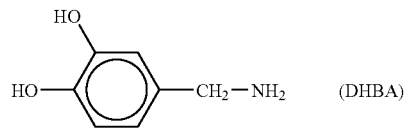

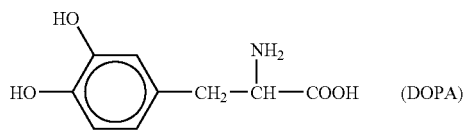

The primary amino group in DHBA or DOPA is chemically active and can be used for conjugating a non-fouling moiety with the molecule of DHBA or DOPA to form a non-fouling, biocompatible stent coating. For example, hyaluronic acid can be attached to the molecule of DHBA or DOPA (or the ethyl ester of DOPA) using the following synthetic scheme. Hyaluronan can be combined with an excess of the amine at pH approximately 6.8 in the presence of a soluble carbodiimide and 1-hydroxybenzotriazole in aqueous dimethylsulfoxide. A water soluble carbodiimide such as 1-ethyl-3(3-dimethylaminopropyl)carbodiimide, also known as carbodiimide or EDC, having the formula $CH_3—CH_2—N=C=N—CH_2—CH_2—CH_2—N(CH_3)_2$ can be used. EDC is manufactured by Pierce Corp., of Rockford, Ill. 1-hydroxybenzotrialzole can be obtained from Aldrich Chemical, of Milwaukee, Wis. By choosing an appropriate ratio between hyaluronan and DHBA or DOPA, those having ordinary skill in the art can attach more than one molecule of DHBA or DOPA to each molecule of hyaluronic acid, if desired.

In case PEG is selected as the non-fouling moiety, the amino group can be also utilized for conjugating PEG to a DHBA or DOPA-based chelate structure. To this end, PEG-succinimidyl propionate can be used. Those having ordinary skill in the art can determine particular chemical pathways for conjugating heparin, PVP and other non-fouling moieties described above.

II. Primers for Stent Coatings Including the Chelating Structures

In addition to enabling the inclusion of non-fouling moieties, group X can also be used to conjugate compound (I) to a polymer to form a macromolecular (polymeric) adduct. The polymeric adduct can be used as a primer for the stent coating. Such polymeric adduct is expected to have improved adhesion to the metal surface of the stent compared to the same polymer without the chelating moiety (I).

Those having ordinary skill in the art can graft compound (I) at multiple locations along the polymer backbone. Grafting along the polymer backbone can be expected to facilitate greater adhesive interaction with the metal surface. Alternatively, compound (I) can be attached to a terminus of the polymer. Examples of suitable polymers to which compound (I) can be conjugated include (a) poly(methacrylates) and poly(acrylates), e.g., poly(butyl methacrylate), poly(ethyl methacrylate), or poly(methyl methacrylate);

(b) polymers derived from monomers having vinyl groups, e.g., poly(vinyl alcohol), poly(ethylene-co-vinyl alcohol), poly(ethyl acetate-co-vinyl alcohol), poly(vinyl acetate), poly(ethylene-co-vinyl acetate), poly(styrene-co-ethylene), poly(styrene-co-tert-butylene), or poly(vinylbutyral);

(c) silicon-containing polymers, e.g., poly(dimethyl siloxane) or silicones;

(d) fluorinated polymers, e.g., poly(tetrafluoroethylene), poly(vinyl fluoride), poly(vinylidene fluoride), poly(ethylene-co-tetrafluoroethylene), or poly(vinylidene fluoride-co-hexafluoropropene);

(e) block copolymers, e.g., poly(styrene-block-co-ethylene-block-co-butylene), or poly(styrene-block-co-butadiene-block-co-styrene); and (f) polymers having functional groups, e.g., polyurethanes, or polyamides.

To form a polymeric adduct, the amino group of DHBA or DOPA can be utilized for conjugating a polymer to a chelating moiety. As one example of conjugating, DHBA or DOPA may be reacted with methacryloyl chloride to make the methacrylate derivative of DHBA or DOPA. The methacrylate derivative can then be copolymerized with other methacrylates, such as butyl methacrylate, to make a poly(butyl methacrylate) primer having the enhanced adhesive properties provided by DHBA or DOPA.

To fabricate a stent coating using a polymeric adduct described above, a polymer solution can be prepared by dissolving the polymeric adduct in a suitable solvent. The polymer solution can be applied onto a bare stent by a commonly used methods, such as spraying or dipping, and the solvent can then be allowed to evaporate, leaving on the stent surface a primer layer. An optional drug-polymer-layer (also referred to as "reservoir" or "reservoir layer") serving as a reservoir for one or more therapeutic substances can be then fabricated. To make a reservoir layer, a composition comprising a solution of a suitable polymer and at least one therapeutic substance dispersed in the polymer solution can be prepared. The composition can then be applied over the primer layer, for example, by spraying, and the solvent can then be allowed to evaporate, leaving the reservoir layer disposed over the primer layer. An optional topcoat layer, which can be essentially free from any therapeutic substances can then be applied in a similar manner over the reservoir layer. The topcoat layer serves as a rate limiting membrane controlling the rate of release of the drug from the reservoir layer.

Examples of suitable polymers that can be used for fabricating the reservoir layer and/or the topcoat layer include poly(ethylene-co-vinyl alcohol), poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), poly(glycerol-sebacate), polyphosphoester, polyphosphoester urethane; poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, other polycarbonates, polyoxymethylenes, polyimides, polyethers, epoxy resins, other polyurethanes, rayon, rayon-triacetate, cellulose, cellulose acetate, cellulose butyrate, cellulose acetate butyrate, cellophane, cellulose nitrate, cellulose propionate, cellulose ethers, soluble fluorinated polymers and carboxymethyl cellulose.

The therapeutic substance which can be used in the reservoir layer can include any substance capable of exerting a therapeutic or prophylactic effect for a patient. The therapeutic substance may include small molecule substances, peptides, proteins, oligonucleotides, and the like. The therapeutic substance could be designed, for example, to inhibit the activity of vascular smooth muscle cells. It can be directed at inhibiting abnormal or inappropriate migration and/or proliferation of smooth muscle cells to inhibit restenosis.

Examples of therapeutic substances that can be used for fabricating the optional reservoir layer include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$ actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.). Examples of such cytostatic or antiproliferative agents include angiopeptin, angiotensin converting enzyme inhibitors such as captopril (e.g. Capoten® and Capozide from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

The embodiments of the present invention are described in connection with a stent, e.g., balloon expandable or self-expandable stenis; however, other implantable medical devices can also be used. Examples of such implantable devices include stent-grafts, grafts (e.g., aortic grafts), artificial heart valves, cerebrospinal fluid shunts, pacemaker electrodes, and endocardial leads (e.g., FINELINE and ENDOTAK, available from Guidant Corp. of Santa Clara, Calif.). The underlying structure of the device can be of virtually any design. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Some embodiments of the present invention can be further illustrated by the following examples.

EXAMPLE 1

A stent can be immersed in a buffered aqueous solution of DHBA for about 1 hour at ambient temperature to form a chelate structure (VI) on the stent. A phosphate buffer having pH about 7.4 can be used. The molar concentration of phosphate in the buffer solution can be about 10 mmol/l.

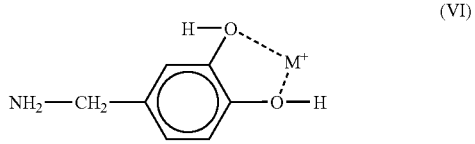

(VI)

Hyaluronic acid can be conjugated to the chelate structure (VI). Hyaluronic acid, also known as poly(β-glucuronic acid-[1→3])-co-β-N-acetylglucosamine-[1→4]) is a linear polysaccharide composed of disaccharide units of N-acetylglucosamine and D-glucuronic acid. In hyaluronic acid, uronic acid and the aminosugar are linked by alternating β-1,4 and β-1,3 glucosidic bonds. Hyaluronic acid has hydroxyl, hydroxymethyl, carboxyl, and amide groups.

A pathway for the process of conjugating hyaluronic acid to the chelate structure (VI) is expected to be a reaction of condensation of carboxyl, hydroxyl, or hydroxymethyl groups of hyaluronic acid with the primary amino group of the chelate structure (VI). The final product of conjugation is expected to contain primarily a compound of formula (III), where X is a product of conjugation of hyaluronic acid to the methylamino group.

To facilitate conjugation of hyaluronic acid to the chelate structure (VI), an appropriate coupling agent may be needed in presence of which the conjugation can be carried. Examples of suitable coupling agents include EDC. Hyaluronic acid can be conjugated to the chelate (VI) by addition of EDC and 1-hydroxybenzotriazole at a pH of about 6.8. The process of conjugation can be carried in aqueous dimethyl sulfoxide at ambient temperature for about 1 hour.

EXAMPLE 2

Poly(ethylene glycol) (PEG) can be conjugated to DHBA. For example, DHBA can be reacted with methoxylated PEG succinimidyl propionate (mPEG-SPA) available from Nektar (formerly Shearwater Corp.) of Huntsville Ala. The structure of mPEG-SPA includes a relatively labile N—O bond which is susceptible to nucleophilic substitution.

Since the succinimidyl group is an excellent electrophile and leaving group, it is expected to be attacked by the nucleophilic lone electron pair of the primary amino group of the chelate structure (VI). As a result, mPEG is conjugated to the chelate structure via an amide bond, and N-hydroxysuccinimide will be released as a by-product of the reaction. One possible path of conjugation can be as illustrated by the reaction scheme (VII):

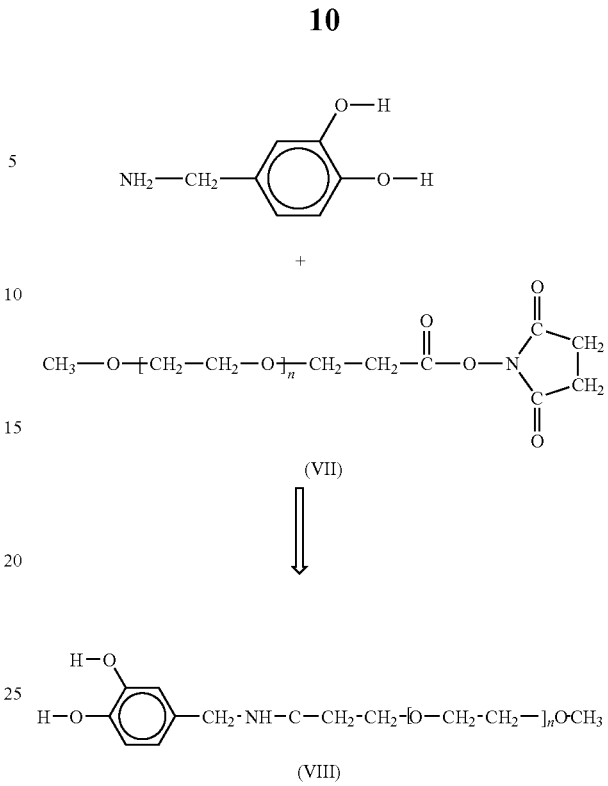

Those having ordinary skill in the art can choose appropriate conditions for carrying out reaction (VII). For example, the reaction can be conduct at a pH of about 8 in water or acetone/water blend, at ambient temperature for about 1 hour. An excess of mPEG-SPA can be used. After the reaction (VII) has been completed, the resulting adduct (VIII) can be purified by dialysis to remove N-hydroxysuccinimide and isolated by lyophilization or salt precipitation.

Adduct (VIII) can then be reacted with the stent. To react adduct (VIII) with the stent, the clean stent can be exposed to adduct (VIII) in a phosphate buffer having pH about 7.4 for about 1 hour at ambient temperature. The molar concentration of phosphate in the buffer solution can be about 10 mmol/l.

EXAMPLE 3

The chelate structure (VI) can be formed on a stent as described above. Heparin can then be conjugated to the chelate structure (VI). To conjugate heparin, first heparin can be partially degraded with nitrous acid, thus obtaining compound comprising a heparin-derived moiety having terminal aldehyde groups. This compound can be schematically shown as HEP-C(O)H, where HEP is a heparin moiety. The aldehyde groups are easily reacted with the primary amino groups of the chelate structure, as shown by the reaction scheme (IX), to form the Shiff's base (X) which includes imino groups:

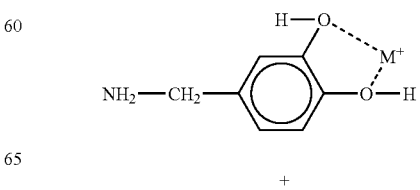

+

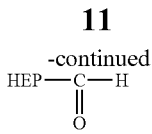

(IX)

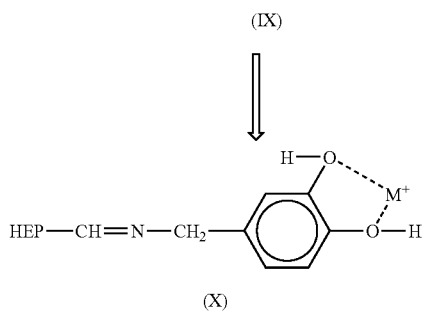

(X)

The Shiff's base (X) can be reduced, for example, by reacting with sodiumborohydride, NaCNBH$_4$, to form a structure where heparin is conjugated to the chelate structure (V).

Aldehyde terminated heparin used to conduct reaction (IX) may be obtained by combining heparin in an aqueous solution of 10% acetic acid and 0.25 mol/l aqueous solution of NaNO$_2$ at room temperature for about 20 minutes. The solution can be neutralized to pH of about 5 with sodium hydroxide and dialyzed.

To conduct the reaction of reductive amination (IX), the chelated metal surface can be immersed in an aqueous solution of the HEP-C(O)H with sodium cyanoborohydride in absolute ethanol and with 1% aqueous acetic acid and incubated at a temperature of about 60° C. for about 1 hour.

EXAMPLE 4

A coating can be formed on a stent, the coating comprising a primer layer deposited over the bare stent and a drug polymer layer deposited over the primer layer. The primer layer includes a polymeric adduct. To obtain the polymeric adduct, 3,4-dihydroxybenzylmethacrylamide can be made synthetically first.

3,4-dihydroxybenzylmethacrylamide can be synthesized according to the following procedure. About 1 equivalent of 3,4-dihydroxybenzylamine can be combined with two equivalents of pyridine hydrobromide. Both components can be preliminarily dissolved in a suitable solvent to be selected by those having ordinary skill in the art, for example, in toluene. About 1 equivalent of methacryloyl chloride can then be added dropwise with stirring at room temperature to carry out reaction (XI):

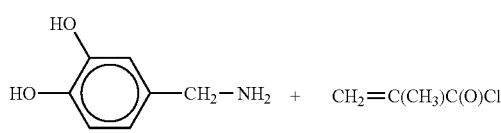

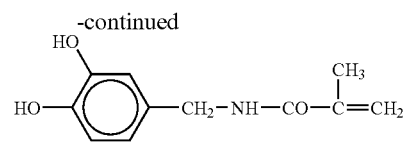

(XI)

After about two hours of continued stirring, 3,4-dihydroxybenzylmethacrylamide, the product of reaction (XI) can be isolated by extracting the organic phase with three portions of diethyl ether. The three ether fractions can be combined and extracted with two portions of water, followed by drying in a desiccator over anhydrous magnesium sulfate to obtain 3,4-dihydroxybenzylmethacrylamide.

1 equivalent of 3,4-dihydroxybenzylmethacrylamide can be combined with 19 equivalents of n-butylmethacrylate in 2-butanone. Under a blanket of nitrogen, a free radical copolymerization can be initiated by addition of about 0.15 mass % of benzoyl peroxide and allowing the reaction schematically shown as reaction (XII) to proceed at about 80° C. for about 12 hours to yield copolymer (XIII):

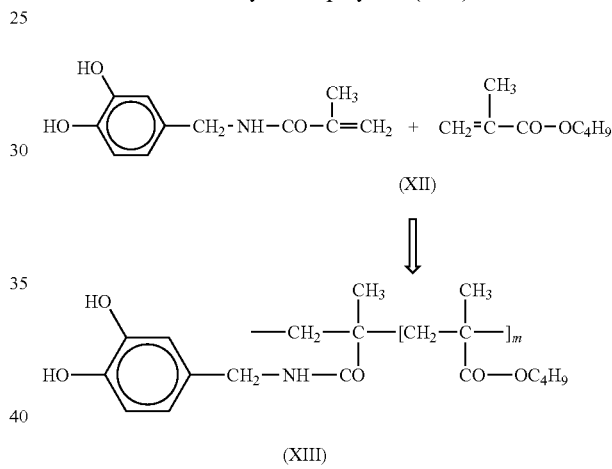

The product of copolymerization (XIII) can be isolated by precipitation with methanol and purified by repeated dissolution in 2-butanone followed by precipitation with methanol. Drying in vacuum at about 60° C. for about 12 hours completes the isolation of a polymeric adduct. The adduct is expected to include primarily poly(n-butylmethacrylate) terminated on one end with a derivative of 3,4-dihydroxybenzene. The adduct can be used as a primer for a stent coating.

A formulation of polymeric adduct (XIII) can be prepared, the formulation to include:

(a) about 2 mass % polymeric adduct (XIII); and (b) a balance, a solvent blend comprising acetone and xylene in a mass ratio of about 1:1.

The formulation of polymeric adduct (XIII) can be applied to an 18 mm VISION stent (available from Guidant Corporation) to form a primer coating layer on the stent. A series of 10-second passes can be used, to deposit, for example, 10 µg of coating per spray pass. Between the spray passes, the stent can be dried for about 10 seconds using flowing air with a temperature of about 60° C. Ten spray passes can be applied, followed by baking the primer layer at about 140° C. for one hour. As a result, a primer layer can be formed having a solids content of about 100 µg.

"Solids" means the amount of the dry residue deposited on the stent after all volatile organic compounds (e.g., the solvent) have been removed.

A drug-containing formulation can be prepared comprising:

(a) between about 0.1 mass % and about 15 mass %, for example, about 2.0 mass % of poly(vinylidene fluoride-co-hexafluoropropene) (VDF-HFP);

(b) between about 0.1 mass % and about 2 mass %, for example, about 1.6 mass % of EVEROPLIMUS; and (c) a balance, a solvent blend comprising acetone and cyclohexanone in a mass ratio of about 1:1.

In a manner identical to the application of the primer layer, five spray passes can be performed, followed by baking the drug-polymer layer at about 50° C. for about 1 hour, to form the drug-polymer layer having a solids content between about 30 µg and 750 µg, for example, about 360 µg.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable medical device, comprising a compound chemically coordinated with a surface of the implantable medical device, wherein the compound includes:
   (a) a moiety capable of forming a chelate structure with a metal or a metal oxide; and
   (b) a non-fouling moiety, conjugated to the moiety capable of forming a chelate structure,
   wherein the moiety capable of forming a chelate structure includes a compound having the formula:

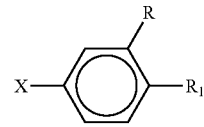

where one of R and $R_1$ is selected from hydroxyl, mercapto, phosphine, alkylphosphine, primary amino, secondary amino, tertiary amino, and carboxyl groups and the other of R and $R_1$ is selected from mercapto, phosphine, alkylphosphine, primary amino, secondary amino, tertiary amino, and carboxyl groups; and
   wherein X is a reactive group.

* * * * *